US011161796B2

(12) United States Patent
Leal et al.

(10) Patent No.: US 11,161,796 B2
(45) Date of Patent: Nov. 2, 2021

(54) SYSTEMS AND PROCESSES FOR EFFICIENT PRODUCTION OF ONE OR MORE FUEL ADDITIVES

(71) Applicant: SABIC Global Technologies B.V., Bergen op Zoom (NL)

(72) Inventors: Guillermo Leal, Riyadh (SA); Mohammed Bismillah Ansari, Riyadh (SA); Vijay Dinkar Bodas, Riyadh (SA); Sultan Eid Al-Otaibi, Riyadh (SA); Mohammed A. Al-Ghamdi, Riyadh (SA); Naif Mohammed Al-Naddah Al-Otaibi, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/264,430

(22) PCT Filed: Sep. 16, 2019

(86) PCT No.: PCT/IB2019/057784
§ 371 (c)(1),
(2) Date: Jan. 29, 2021

(87) PCT Pub. No.: WO2020/058825
PCT Pub. Date: Mar. 26, 2020

(65) Prior Publication Data
US 2021/0246088 A1 Aug. 12, 2021

Related U.S. Application Data

(60) Provisional application No. 62/732,751, filed on Sep. 18, 2018.

(51) Int. Cl.
| | | |
|---|---|---|
| *C07C 5/00* | (2006.01) | |
| *C07C 7/00* | (2006.01) | |
| *C07C 29/04* | (2006.01) | |
| *C07C 5/05* | (2006.01) | |
| *C07C 7/04* | (2006.01) | |

(52) U.S. Cl.
CPC .............. *C07C 5/05* (2013.01); *C07C 7/04* (2013.01); *C07C 29/04* (2013.01)

(58) Field of Classification Search
CPC .............. C07C 5/05; C07C 7/04; C07C 29/04
See application file for complete search history.

(56) References Cited

U.S. PATENT DOCUMENTS

| | | |
|---|---|---|
| 3,797,690 A | 3/1974 | Taylor et al. |
| 3,849,082 A | 11/1974 | Kozlowski et al. |
| 3,912,463 A | 10/1975 | Kozlowski et al. |
| 4,334,890 A | 6/1982 | Kochar et al. |
| 4,336,046 A | 6/1982 | Schorre et al. |
| 4,356,339 A | 10/1982 | Imaizumi et al. |
| 4,408,085 A | 10/1983 | Gottlieb et al. |
| 4,423,251 A | 12/1983 | Pujado et al. |
| 4,455,445 A | 6/1984 | Neuzil et al. |
| 4,499,313 A | 2/1985 | Okumura et al. |
| 4,540,831 A | 9/1985 | Briggs |
| 4,773,968 A | 9/1988 | O'Connell et al. |
| 4,783,555 A | 11/1988 | Atkins |
| 4,797,133 A | 1/1989 | Pujado |
| 4,927,977 A | 5/1990 | Child et al. |
| 5,227,553 A | 7/1993 | Polanek et al. |
| 5,254,748 A | 10/1993 | Hensley et al. |
| 5,382,707 A | 1/1995 | Rubin et al. |
| 5,523,502 A | 6/1996 | Rubin |
| 5,563,299 A | 10/1996 | Paludetto et al. |
| 5,628,880 A | 5/1997 | Hearn et al. |
| 5,898,091 A | 4/1999 | Chodorge et al. |
| 5,955,640 A | 9/1999 | Paludetto et al. |
| 7,227,047 B2 | 6/2007 | Risch et al. |
| 7,473,812 B2 | 1/2009 | Peters et al. |
| 7,485,761 B2 | 2/2009 | Schindler et al. |

(Continued)

FOREIGN PATENT DOCUMENTS

| | | |
|---|---|---|
| CN | 1044804 C | 8/1999 |
| CN | 1506344 A | 6/2004 |

(Continued)

OTHER PUBLICATIONS

Ansari et al.; U.S. Appl. No. 17/054,906; entitled "Method of Producing a Fuel Additive With a Hydration Unit"; filed Nov. 12, 2020.
Bodas et al.; U.S. Appl. No. 17/292,261; entitled "Process and System for Producing Ethylene and at Least One of Butanol and an Alkyl Tert-Butyl Ether"; filed May 7, 2021.
Leal et al. U.S. Appl. No. 17/052,407, entitled "Method of Producing a Fuel Additive", filed Nov. 2, 2020.
International Search Report for International Application No. PCT/IB2019/059984; International Filing Date Nov. 20, 2019; dated Feb. 21, 2020; 5 pages.

(Continued)

*Primary Examiner* — Sikarl A Witherspoon
(74) *Attorney, Agent, or Firm* — Cantor Colburn LLP

(57) ABSTRACT

A method for the production of a fuel additive includes passing a hydrocarbon stream comprising crude mixed C4 hydrocarbons through a first hydrogenation unit to produce a first product stream; passing the first product stream from the first hydrogenation unit to a methyl tert-butyl ether synthesis unit forming methyl tert-butyl ether and a byproduct stream; passing the byproduct stream through a first distillation unit to separate the byproduct stream into a first 1-butene stream, an isobutane stream, and a 2-butene and n-butane stream; forming a second product stream by passing the 2-butene and n-butane stream to a selective conversion unit; passing the second product stream into a second distillation unit to form an n-butane stream and a second 1-butene stream; passing the second 1-butene stream to a fuel additive production unit; and passing the first 1-butene stream to the fuel additive production unit to form the fuel additive.

15 Claims, 1 Drawing Sheet

(56) References Cited

U.S. PATENT DOCUMENTS

| | | |
|---|---|---|
| 8,124,572 B2 | 2/2012 | Miller |
| 8,395,007 B2 | 3/2013 | Wright et al. |
| 8,999,013 B2 | 4/2015 | Xu et al. |
| 9,187,388 B2 | 11/2015 | Arjah et al. |
| 9,611,192 B2 | 4/2017 | Digiulio |
| 10,774,020 B2 | 9/2020 | Di Girolamo et al. |
| 2002/0169346 A1 | 11/2002 | Commereuc et al. |
| 2003/0158429 A1 | 8/2003 | Albiez et al. |
| 2007/0265483 A1 | 11/2007 | Himelfarb |
| 2011/0040133 A1 | 2/2011 | Vermeiren et al. |
| 2011/0230632 A1 | 9/2011 | Abhari |
| 2012/0117862 A1 | 5/2012 | Xu |
| 2013/0072732 A1 | 3/2013 | Breuil et al. |
| 2013/0104449 A1 | 5/2013 | Xu et al. |
| 2013/0331620 A1 | 12/2013 | Abhari |
| 2014/0039226 A1 | 2/2014 | Xu et al. |
| 2014/0142350 A1 | 5/2014 | Weiner et al. |
| 2015/0225320 A1 | 8/2015 | Shaik et al. |
| 2015/0322181 A1 | 11/2015 | Kim et al. |
| 2016/0326079 A1 | 11/2016 | Lee et al. |
| 2017/0198231 A1 | 7/2017 | Xu et al. |
| 2020/0157450 A1 | 5/2020 | Leal et al. |
| 2021/0002185 A1 | 1/2021 | Leal et al. |
| 2021/0024837 A1 | 1/2021 | Leal et al. |
| 2021/0024843 A1 | 1/2021 | Leal et al. |
| 2021/0155862 A1 | 5/2021 | Leal et al. |

FOREIGN PATENT DOCUMENTS

| | | |
|---|---|---|
| CN | 101279879 A | 10/2008 |
| CN | 102070391 A | 5/2011 |
| CN | 105585411 A | 5/2016 |
| CN | 106608791 A | 5/2017 |
| CN | 102372573 A | 3/2021 |
| EP | 0063813 B1 | 11/1982 |
| EP | 0102840 B1 | 3/1984 |
| EP | 0253679 | 1/1988 |
| EP | 0605822 A1 | 7/1994 |
| GB | 1374368 | 11/1974 |
| JP | S5920232 A | 2/1984 |
| RU | 2470905 C1 | 12/2012 |
| WO | 9011268 | 10/1990 |
| WO | 9732838 A1 | 9/1997 |
| WO | 0043336 A1 | 7/2000 |
| WO | 0146095 A1 | 6/2001 |
| WO | 2006113191 A2 | 10/2006 |
| WO | 2007024733 A2 | 3/2007 |
| WO | 2012095744 A2 | 7/2012 |
| WO | 2014160825 A1 | 10/2014 |
| WO | 2015089005 A1 | 6/2015 |
| WO | 2015123026 A1 | 8/2015 |
| WO | 2019207477 A1 | 10/2019 |

OTHER PUBLICATIONS

Written Opinion for International Application No. PCT/IB2019/059984; International Filing Date Nov. 20, 2019; dated Feb. 21, 2020; 8 pages.

Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.

International Search Report for International Application No. PCT/IB2019/052177; International Filing Date Mar. 18, 2019; dated Jun. 26, 2019; 3 pages.

International Search Report for International Application No. PCT/IB2019/052178; International Filing Date Mar. 18, 2019; dated Jun. 26, 2019; 6 pages.

International Search Report for International Application No. PCT/IB2019/053697; International Filing Date May 6, 2019; dated Aug. 28, 2019; 11 pages.

International Search Report for International Application No. PCT/US2019/026985; International Filing Date Apr. 11, 2019; dated May 27, 2019; 6 pages.

International Search Report for International Application No. PCT/US2019/028092; International Filing Date Apr. 18, 2019; dated Jun. 26, 2019; 6 pages.

International Search Report for International Application No. PCT/US2019/028099; International Filing Date Apr. 18, 2019; dated Jun. 26, 2019; 6 pages.

International Search Report; International Application No. PCT/IB2018/055647; International Filing Date: Jul. 27, 2018; dated Oct. 30, 2018; 6 pages.

Streich et al.; "Secure the Best Benefits from C4 Hydrocarbon Processing—Part 1: Separation Sequences"; Hydrocarbon Processing: Process Engineering and Optimization; 2016; 6 pages.

Written Opinion for International Application No. PCT/IB2019/052177; International Filing Date Mar. 18, 2019; dated Jun. 26, 2019; 9 pages.

Written Opinion for International Application No. PCT/IB2019/052178; International Filing Date Mar. 18, 2019; dated Jun. 26, 2019; 9 pages.

Written Opinion for International Application No. PCT/IB2019/053697; International Filing Date May 6, 2019; dated Aug. 28, 2019; 9 pages.

Written Opinion for International Application No. PCT/US2019/026985; International Filing Date Apr. 11, 2019; dated May 27, 2019; 7 pages.

Written Opinion for International Application No. PCT/US2019/028092; International Filing Date Apr. 18, 2019; dated Jun. 26, 2019; 9 pages.

Written Opinion for International Application No. PCT/US2019/028099; International Filing Date Apr. 18, 2019; dated Jun. 26, 2019; 13 pages.

Written Opinion; International Application No. PCT/IB2018/055647; International Filing Date: Jul. 27, 2018; dated Oct. 30, 2018; 11 pages.

Brockwell et al.; "Synthesize ethers"; Hydrocarbon Processing, vol. 70, No. 9; 1991; pp. 133-141.

International Search Report for International Application No. PCT/IB2019/057784; International Filing Date Sep. 16, 2019; dated Jan. 7, 2020; 5 pages.

Izquierdo et al.; "Equilibrium Constants for Methyl tert-Butyl Ether Liquid-Phas Synthesis"; J. Chem. Eng. Data, vol. 37; 1992; pp. 339-343.

Kalamaras et al.; "SuperButol—A novel high-octane gasoline blending component"; Fuel, vol. 195; 2017; pp. 165-173.

Written Opinion for International Application No. PCT/IB2019/057784; International Filing Date Sep. 16, 2019; dated Jan. 7, 2020; 7 pages.

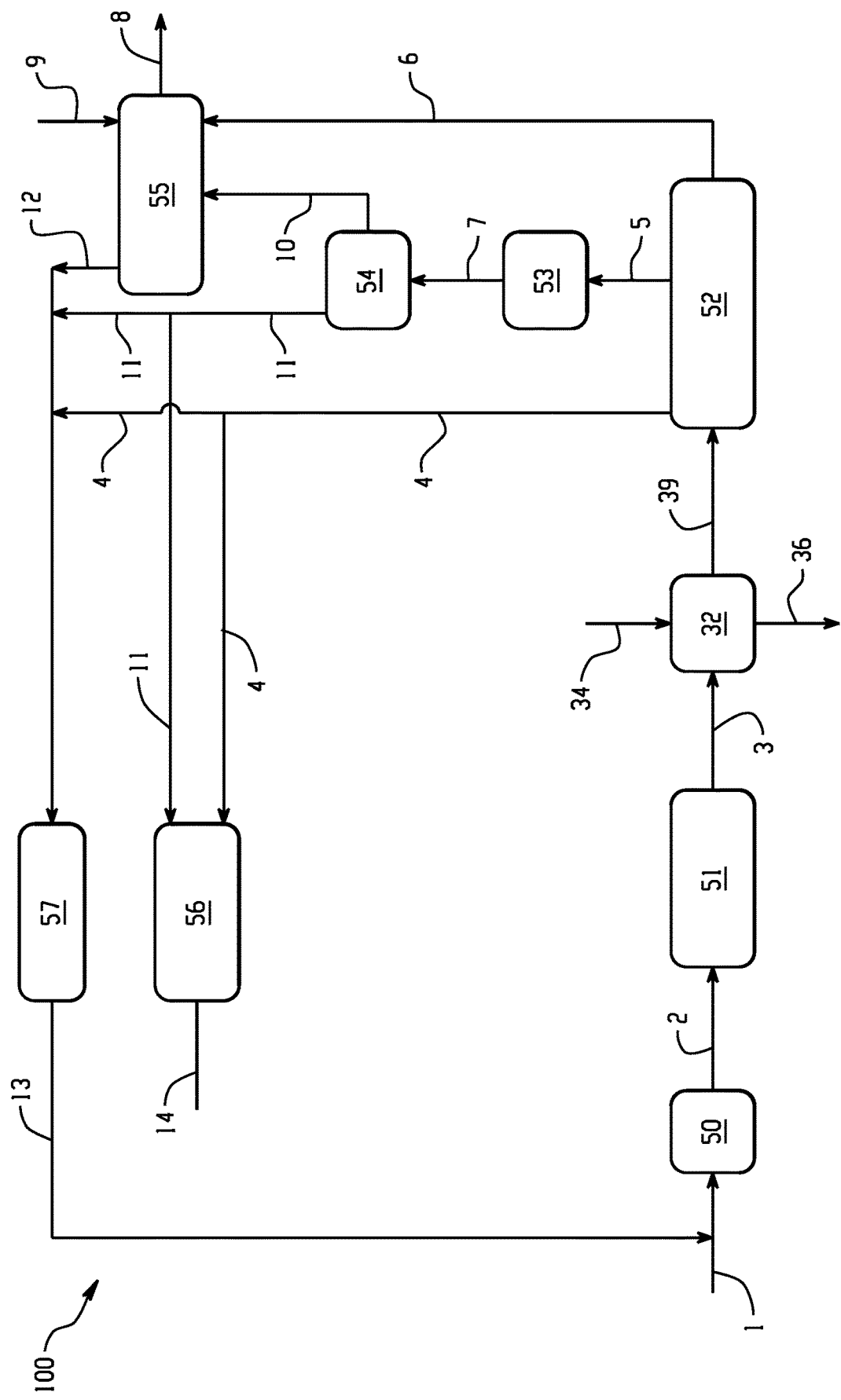

SYSTEMS AND PROCESSES FOR EFFICIENT PRODUCTION OF ONE OR MORE FUEL ADDITIVES

CROSS REFERENCE TO RELATED APPLICATIONS

This application is a National Stage application of PCT/IB2019/057784, filed Sep. 16, 2019, which is incorporated herein by reference in its entirety, and which claims the benefit of U.S. Provisional Application No. 62/732,751, filed Sep. 18, 2018.

BACKGROUND

Commercial gasoline, which is fuel for internal combustion engines, is a refined petroleum product that is typically a mixture of hydrocarbons (base gasoline), additives, and blending agents. Additives and blending agents are added to the base gasoline to enhance the performance and the stability of gasoline, and can include anti-knock agents, anti-oxidants, metal deactivators, lead scavengers, anti-rust agents, anti-icing agents, upper-cylinder lubricants, detergents, and dyes.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline. Prior octane boosters such as tetraethyl lead and methylcyclopentadienyl manganese tricarbonyl (MMT) have been or are being phased out for environmental, health, or other reasons.

Methyl tert-butyl ether (MTBE) is an aliphatic alkyl ether that is used as a gasoline additive to increase the octane rating of gasoline products. Typically, MTBE is produced on a large scale by reaction of isobutene with methanol according to reaction (I)

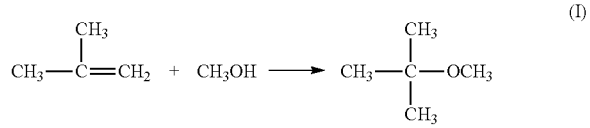

One major challenge in refinery and petrochemical arts is to achieve the required purity and volume to match the commercial targets of different products, such as fuel additives.

In the case of a mixed C4 hydrocarbons stream, such as an effluent stream from a cracker, the components of the stream can be valuable and can include components such as n-butane, 1-butene, 2-butene, isobutane, and isobutene. The separation of each of these components presents a technical and financial challenge. The utilization of isobutene, n-butane, 1-butene, and 2-butene individually from the effluent stream of a cracker can increase the financial benefits of the original mixed C4 stream from the cracker.

In view of the foregoing, there remains a need to provide cost-effective methods of separating the 1-butene and 2-butene from the C4 effluent stream of a cracker for use as a fuel additive, such as methyl-tert butyl ether and/or trimethylpentane.

SUMMARY

Disclosed, in various embodiments, are systems and processes for efficient production of one or more fuel additives.

A method for the production of a fuel additive comprises: passing a stream comprising crude mixed C4 hydrocarbons from one or more crackers through a first hydrogenation unit to convert butadiene components to 1-butene and 2-butene to produce a first product stream; passing the first product stream from the first hydrogenation unit to a methyl tert-butyl ether synthesis unit forming methyl tert-butyl ether and a byproduct stream; passing the byproduct stream through a first distillation unit to separate the byproduct stream into at least three streams including a first 1-butene stream, an-isobutane stream, and a 2-butene and n-butane stream; forming a second product stream by passing the 2-butene and n-butane stream to a selective conversion unit to transform the 2-butene to 1-butene; passing the second product stream into a second distillation unit to separate the n-butane from the 1-butene to form an n-butane stream and a second 1-butene stream; passing the second 1-butene stream to a fuel additive production unit to form the fuel additive; and passing the first 1-butene stream to the fuel additive production unit to form the fuel additive.

These and other features and characteristics are more particularly described below.

BRIEF DESCRIPTION OF THE DRAWING

The following is a brief description of the drawing wherein like elements are numbered alike and which is presented for the purposes of illustrating the exemplary embodiments disclosed herein and not for the purposes of limiting the same.

FIG. 1 is a block diagram of the processes disclosed herein.

These and other features and characteristics are more particularly described below.

DETAILED DESCRIPTION

Disclosed herein is an improved method of producing a fuel additive. Specifically, in various embodiments, efficient processes for the production of fuel additives such as C4 alcohols, methyl-tert butyl ether (MTBE), trimethylpentane, C4 dimers, or a combination comprising at least one of the foregoing are disclosed. The processes disclosed herein are efficient in the production of fuel additives because the processes can maximize the use of an effluent stream from a cracker.

Disclosed herein are novel methods and systems for purifying and separating crude C4 streams to produce streams that can be used as input streams for the synthesis of fuel additives such as C4 alcohols, methyl-tert butyl ether (MTBE), C4 dimers, trimethylpentane, or a combination comprising at least one of the foregoing. In comparison to current methods and systems, the method described herein offers lower cost, higher efficiency, and more flexible methods for utilizing the components of a crude C4 stream.

The present method provides, among other things, new processes and systems for separating and purifying C4 fractions from a crude C4 stream. The processes disclosed herein can simplify the C4 separation processes, afford more possible configurations for separation and purification, and be more cost effective. Accordingly, the processes and systems provided herein can be used as part of a cost-effective and efficient method for synthesizing fuel additives, wherein the final fuel additive products can have levels of 2-butanol, tert-butyl alcohol, C4-dimer, or a combination comprising at least one of the foregoing. For example, the final fuel additive products can have levels of the C4-dimer comprising trimethyl-pentane, di-isobutene, 2,2,4 trimethyl-pentane, 2,3,3 trimethyl-pentane, or a combination comprising at least one of the foregoing in an amount of 0.01 weight percent (wt %) to 50 wt %, based on the total weight of the fuel additive; the final fuel additive products can have high octane numbers (e.g., greater than or equal to 85 Research Octane Number (RON), or greater than or equal to 87 RON); and the final fuel additive products can have low Reid vapor pressures of less than or equal to 55 KiloPascals (8.0 pounds per square inch (psi)). For example, the trimethyl-pentane can be present in an amount of 0.1 to 25 weight percent, for example, 1 to 20 wt %. Any one or all of these properties can correlate with high performance and high market value. The method disclosed herein can also produce secondary products along with the fuel additive product. For example, ethylene and propylene products can be produced through the steam crackers, thereby enhancing the efficiency and productivity of the process. Furthermore, the methods disclosed herein can also permit the separation of normal butane from isobutylene and then the recycling of the normal butane to the cracker, thereby providing a feed stream to the cracker that is more efficiently processed, giving rise to productivity and associated cost benefits.

The method can include, for example, passing a stream comprising crude mixed C4 hydrocarbons through a hydrogenation unit such as a selective hydrogenation unit to convert butadiene components to 1-butene and 2-butene, passing a first product stream including 1-butene and 2-butene to an MTBE synthesis unit creating a byproduct stream and passing that byproduct stream to a first distillation unit to separate into at least three streams including a first 1-butene stream, an isobutane stream, and a 2-butene and n-butane stream. The first 1-butene stream and the isobutane stream may each contain trace amounts of isobutene. A second product stream is then formed by passing the 2-butene and n-butane stream to a selective conversion unit to transform the 2-butene to 1-butene, passing the second product stream into a second distillation unit to separate n-butane from 1-butene, passing the resulting second 1-butene stream to a fuel additive production unit, and passing the first 1-butene stream to the fuel additive production unit and forming the fuel additive.

In the processes disclosed herein, any mixed C4 hydrocarbon stream can be used as a feedstock. The mixed C4 hydrocarbons can be drawn from a variety of sources, including, but not limited to, crackers (e.g., fluid catalytic crackers) in refineries, or crude C4's from crackers in petrochemical units. For example, a portion of an effluent from an olefins production plant, or a stream from a cracker can be used as a feedstock. For example, the mixed C4 hydrocarbon stream can comprise ethyl acetylene, vinyl acetylene, 1,3-butadiene, 1,2-butadiene, isobutene, cis-2-butene, trans-2-butene, 1-butene, isobutane, n-butane, or a combination comprising at least one of the foregoing. The mixed C4 hydrocarbon stream can comprise less than or equal to 50 weight percent (wt %) butadienes, for example, less than or equal to 45 wt % butadienes, for example, less than or equal to 25 wt % butadienes, for example, less than or equal to 20 wt % butadienes, for example, less than or equal to 15 wt % butadienes. Various exemplary mixed C4 hydrocarbon stream compositions are shown in Table 1.

TABLE 1

Exemplary Feedstock Compositions

| Crude C4 Stream from Cracker<br>C4 Stream Constituents | Example 1<br>wt % | Example 2<br>wt % | Example 3<br>wt % | Example 4<br>wt % |
|---|---|---|---|---|
| $C_4H_6$ (butadiene) | 14.72% | 17.27% | 15.27% | 20.44% |
| 1-$C_4H_8$ (1-butene) | 9.21% | 8.99% | 9.19% | 8.76% |
| 2-$C_4H_8$ (2-butene) | 5.66% | 5.53% | 5.64% | 5.38% |
| iso-$C_4H_8$ (isobutene) | 19.78% | 18.52% | 18.99% | 17.76% |
| $nC_4H_{10}$ (n-butane) | 33.40% | 33.56% | 34.36% | 32.18% |
| $IC_4H_{10}$ (isobutane) | 17.23% | 16.13% | 16.55% | 15.47% |
| Total | 100.00% | 100.00% | 100.00% | 100.00% |
| Tons/hour | 72.380 | 58.206 | 71.323 | 69.036 |

As the skilled artisan will appreciate, the process that is illustrated in FIG. 1 is a highly simplified schematic of the processes described herein. The processes can, and often times will, include additional features that are not shown in FIG. 1. FIG. 1 should in no way be considered to limit the processes disclosed herein.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

A feedstock stream 1 can be passed through a cracker unit 50 (e.g., a steam cracker) producing a cracker output stream 2 and subsequently sent to a first hydrogenation unit 51. The first hydrogenation unit 51 can be a selective hydrogenation unit. For example, the cracker output stream 2 can be a crude C4 stream (e.g., a mixed C4 hydrocarbon stream) from the cracker unit 50. Examples of components in the cracker output stream 2 can include, ethyl acetylene, vinyl acetylene, 1,3-butadiene, 1,2-butadiene, isobutene, cis-2-butene, trans-2-butene, 1-butene, isobutane, n-butane, or a combination comprising at least one of the foregoing.

The first hydrogenation unit 51 can convert a large portion of the butadienes present in the cracker output stream 2 to 1-butene and 2-butene in addition to other alkanes. For example, the first hydrogenation unit 51 can convert 40 wt % to 100 wt % of the butadienes, for example greater or equal to 70 wt % of the butadienes, for example greater than or equal to 90 wt % of the butadienes in the cracker output stream 2. To operate the first hydrogenation unit 51, an output stream, for example, the cracker output stream 2, which typically contains less than or equal to 50 wt % butadienes, for example, less than or equal to 45 wt % butadienes, for example, less than or equal to 25 wt % butadienes, for example, less than or equal to 20 wt % butadienes, for example, less than or equal to 15 wt % butadienes can be passed into the first hydrogenation unit 51.

The first hydrogenation unit 51 can be any reactor able to convert the butadienes present in the cracker output stream 2 to 1-butene and 2-butene. For example, the first hydrogenation unit 51 can comprise three reactor stages. For example the first two reactor stages can be of substantially the same type and contain the same catalyst. The first two reactor stages can convert butadiene present in the cracker output stream 2 to 1-butene to 2-butene. The first two reactor stages can comprise a selective hydrogenation catalyst. For example, the hydrogenation catalyst can comprise palladium with an aluminum base. The hydrogenation catalyst can comprise platinum, rhodium, palladium, ruthenium, cobalt, nickel, copper, or a combination comprising at least one of the foregoing. The catalyst can be the same for the first two reactor stages. Hydrogen can optionally be injected into the cracker output stream 2 prior to passing through the first reactor stage.

Optionally, the cracker output stream 2 can be injected with a small amount (e.g., 100-125 parts per million) of tertiary butyl catechol (TBC) and hydrogen and sent to the first reactor stage. After the first reactor stage, additional hydrogen can be added before passing to the second reactor stage. After the second reactor stage, hydrogen is flashed from the effluent, and additional hydrogen and controlled carbon monoxide can be injected before it is passed to the third reactor stage. The third reactor stage is of a different type than either of the first two stages and can contain a different catalyst. Recycle flow from the first and third reactor stages can be routed back to the feeds for those reactor stages.

Final hydrogenation of di-olefins to a desired product of mono-olefin can be achieved in the third reactor. Carbon monoxide can be injected into the third reactor to attenuate the catalyst and minimize the isomerization reaction from 1-butene to 2-butene. During normal operations, the desired carbon monoxide injection rate can be 2 parts per million of the feedstream to the third reactor. The rate can be increased if too much 1-butene is being lost to 2-butene. A hydrogenated stream can then be withdrawn from the hydrogenation unit. Operation conditions for the selective hydrogenation unit are shown in Table 2. Temperature is reported in degrees Celsius and pressure in pounds per square inch gauge and KiloPascals (kPa).

TABLE 2

| Reactor | Temp °C. | Pressure (psig) | Catalyst | Representative butadienes content at exit |
|---|---|---|---|---|
| 1st | 40-70 | 140-400 (965-2758 kPa) | Noble metal/Alumina | 7% |
| 2nd | 50-60 | 140-400 (965-2758 kPa) | Noble metal/Alumina | 1% |
| 3rd | 60-80 | 250-270 (1724-1862 kPa) | Noble metal/Alumina | <0.01% |

As shown in FIG. 1, the first hydrogenation unit 51 can output a first product stream 3. The first product stream 3 can comprise, for example, 1-butene, 2-butene, isobutene, isobutane, n-butane, or a combination comprising at least one of the foregoing. The first product stream 3 can further comprise any remaining butadienes from the cracker output stream 2 that were not converted by the first hydrogenation unit 51. For example, the first product stream 3 can comprise less than or equal to 60 wt % of the butadienes that were present in the cracker output stream 2, e.g., less than or equal to 40 wt %, for example less than or equal to 10 wt %, of the butadienes that were present in the cracker output stream 2.

As shown in FIG. 1, the first product stream 3 from the first hydrogenation unit 51 can then be sent to a MTBE synthesis unit 32. The MTBE synthesis unit 32 can also include a methanol feed 34. Methanol from the methanol feed 34 can enter the MTBE synthesis unit 32 at a flow rate of Z×1.1 to Z×1.8, where Z is equal to the amount of isobutene present in the first product stream 3. Purity of the methanol from the methanol feed 34 can be 98.5 wt % to 99.85 wt %.

The first product stream 3 from the first hydrogenation unit 51 can be the sole source of isobutene for the MTBE synthesis unit 32. Alternatively, the first product stream 3 from the first hydrogenation unit 51 can be combined with or used in conjunction with an additional isobutene feed stream (not shown). For example, an additional isobutene stream can be obtained by conventional dehydrogenation of isobutane to produce an isobutene and an isobutane mixture.

The chemical reaction used to produce MTBE is not particularly limited, and can be a reaction that is compatible with the isobutene-containing feedstream from the cracker unit. In certain embodiments, the chemical reaction used to produce MTBE is a liquid phase reaction of isobutene and methanol catalyzed by cationic ion-exchange resin (see, e.g., Izquierdo, J. F., Cunill, F., Vila M., Tejero J. and Tborra M. Equilibrium constants for methyl tertiary butyl ether liquid-phase synthesis. Journal of Chemical and Engineering Data, 1992, vol. 37, p. 339.; Brockwell, H. L., Sarathy P. R. and Trotta R. Synthesize ethers. Hydrocarbon Processing, 1991, vol. 70, No. 9, p. 133; Chemical Economics Handbook, Gasoline Octane Improvers. CEH Marketing Report, 1986, p. 543, Stanford Research Institute, SRI International, Menlo Park, Calif.).

As shown in FIG. 1, the MTBE synthesis unit 32 can have two primary output streams. One output stream, the MTBE stream 36, can comprise mostly MTBE. For example, the MTBE output stream 36 can comprise greater than or equal to 80 wt % MTBE, for example greater than or equal 90 wt % MTBE, for example greater than or equal to 95 wt % MTBE. The other output stream of the MTBE synthesis unit 32 can be a byproduct stream 39. The byproduct stream 39 can include 1-butene, 2-butene, n-butane, and isobutane (and can also include trace amounts of isobutene). Exemplary amounts for the components of the byproduct stream can include 1-butene in an amount of 0.165 wt %, 2-butene in an amount of 0.209 wt %, n-butane in an amount of 0.417 wt %, and isobutane in an amount of 0.183 wt %. It can be preferred that the isobutene content be less than or equal to 2 wt % and can vary according to the amount of MTBE produced.

Next, the byproduct stream 39 from the MTBE synthesis unit 32 can be fed to a first distillation unit 52. The first distillation unit 52 can be used to separate the byproduct stream 39 into at least three streams. For example, as shown in FIG. 1, the byproduct stream 39 can be separated into a first 1-butene stream 6, an isobutane stream 4, and a 2-butene and n-butane stream 5. The first distillation unit 52 can be a distillation unit able to separate the byproduct stream 39 into desired components. The first distillation unit 52 can be, for example, a distillation column, a reactive distillation column, a catalytic distillation column, or the like. The first distillation unit 52 can comprise one or more distillation columns, for example, two distillation columns, three distillation columns or four distillation columns. The first distillation unit 52 can be operated at a temperature of 20° C. to 120° C. and a pressure of 4 bar to 15 bar (400 kPa to 1,500 kPa).

The distillation can be conducted at various pressures, including reduced pressures, atmospheric pressure, or elevated pressures. In certain embodiments, distillation can be conducted at a reduced pressure, e.g., a pressure of less than 1 bar, e.g., less than 0.5 bar, less than 0.3 bar, less than 0.2 bar, less than 0.1 bar, less than 0.05 bar, less than 0.03 bar, less than 0.02 bar, less than 0.01 bar, or less than 0.01 bar. Distillation can alternatively be conducted at an elevated pressure. For example, distillation can be conducted at a pressure of 1 bar to 4 bar, e.g., at 1 bar, 1.5 bar, 2 bar, 2.5 bar, 3 bar, 3.5 bar, or 4 bar.

The first distillation unit 52 can be constructed of materials including, but not limited to, metals, alloys including steel, glass, enamels, ceramics, polymers, plastics, or a combination comprising at least one of the foregoing.

As shown in FIG. 1, the first distillation unit 52 can have three outputs. For example the first distillation unit 52 can yield a first 1-butene stream 6, an isobutane stream 4, and a 2-butene and n-butane stream 5.

Table 3 lists exemplary components and amounts for the byproduct stream 39, the isobutane stream 4, the n-butane and 2-butene stream 5, and the first 1-butene stream 6.

TABLE 3

Exemplary Stream Components (corresponding to First Distillation Unit 52)

| Stream | Material Balance Weight Fraction | | | |
|---|---|---|---|---|
|  | 39 | 4 | 5 | 6 |
| Phase | Liquid | Liquid | Liquid | Liquid |
| Temperature (° C.) | 46.0 | 55.36 | 68.49 | 60.68 |
| Pressure (bar) | 12.0 | 8.0 | 8.0 | 8.0 |
| Isobutane | 0.183 | 0.949 | 0.000 | 0.001 |
| n-butane | 0.417 | 0.000 | 0.607 | 0.000 |
| 1-butene | 0.165 | 0.030 | 0.078 | 0.879 |
| cis-2-butene | 0.106 | 0.000 | 0.154 | 0.000 |
| trans-2-butene | 0.103 | 0.000 | 0.149 | 0.000 |
| Isobutene | 0.019 | 0.021 | 0.001 | 0.120 |
| 2-methyl-1-butene | 0.007 | 0.000 | 0.010 | 0.000 |
| kg/hr | 70521.00 | 13832.100 | 48572.227 | 8091.518 |

The isobutane stream 4 can comprise at least 0.1 wt % isobutene, for example at least 0.2 wt % isobutene, for example, at least, 0.3 wt % isobutene, or for example, at least 1.0 wt % isobutene. As shown in FIG. 1, the isobutane stream 4 can be sent to an MTBE production unit 56 and/or recycled to a cracker unit 50 (e.g., a cracker unit 50 that can produce ethylene and propylene).

As shown in FIG. 1, the n-butane and 2-butene stream 5 can then be sent to a selective conversion unit 53 to convert 2-butene to 1-butene. In some embodiments, the selective conversion unit 53 is a second hydrogenation unit.

The selective conversion unit 53 can be used to selectively convert 2-butene from the n-butane and 2-butene stream 5 into 1-butene. The selective conversion unit 53 can convert a large portion of the 2-butene present in the n-butane and 2-butene stream 5 to 1-butene, for example the selective conversion unit 53 can convert 40 wt % to 100 wt % of the 2-butene, for example greater than or equal to 70 wt % of the 2-butene, for example greater than or equal to 90 wt % of the 2-butene in the n-butane and 2-butene stream 5. To operate the selective conversion unit 53, a stream 5, for example the n-butane and 2-butene stream 5, which in some embodiments can contain approximately 0.3 wt % 2-butene, can be passed into the unit.

The selective conversion unit 53 can be a reactor able to convert the 2-butene to 1-butene present in the n-butane and 2-butene stream 5. For example, the selective conversion unit 53 can be operated at a pressure of 2 bar to 6 bar and a temperature of 25° C. to 60° C. Hydrogen can be added to the selective conversion unit 53 to assist the hydrogenation of olefins present in the selective conversion unit 53. A catalyst can be present in the selective conversion unit 53. For example, the catalyst can be present in an amount of 0.01 to 1.0 wt %. The catalyst can comprise palladium with an aluminum base. The hydrogenation catalyst can comprise platinum, rhodium, palladium, ruthenium, cobalt, nickel, copper, or a combination comprising at least one of the foregoing or another Group VIII metal.

As shown in FIG. 1, following the selective conversion unit 53, the second product stream 7 that comprises n-butane and 1-butene can be sent to a separation unit 54 (e.g., separation unit 54 taking the form of a second distillation unit 54) to separate the n-butane from 1-butene. The separation unit 54 can have two or more outputs, for example an n-butane stream 11 and a second 1-butene stream 10. The separation unit 54 can be operated at a pressure of 4 bar to 15 bar and a temperature of 20° C. to 120° C. The n-butane stream 11 comprises greater than 95 wt % n-butane, with the remainder being 1-butene and the second 1-butene 10 stream comprises greater than 95 wt % 1-butene, with the remainder being n-butane. The unconverted 2-butene can be present in a recycle stream around the selective conversion unit 53 (not shown).

As shown in FIG. 1, a portion of both the n-butane stream 11 and the isobutane stream 4 can be sent to the MTBE production unit 56 and subjected to various downstream processes in order to form MTBE. For example, the isobutane stream 4 and the n-butane stream 11 can be subjected (as needed) to a de-isobutanizer column to separate n-butane from iso-butane, an isomerization unit, a dehydrogenation unit, and/or a MTBE synthesis unit. The MTBE production unit 56 can include additional inputs, for example, the MTBE production unit 56 can have a methanol feed stream (not shown). Methanol from such a methanol feed can enter the MTBE production unit 56 at a flow rate of Z×1.1 to Z×1.8, where Z is equal to the amount of isobutene present in the feeds to the MTBE production unit 56. Purity of the methanol from the methanol feed 34 can be 98.5 wt % to 99.85 wt %.

The isobutane stream 4 can be combined with or used in conjunction with an additional isobutane feed stream (not shown). For example, an additional isobutane stream can be obtained by conventional isomerization of n-butane as can be obtained from, for example, an n-butane isomerization unit.

As shown in FIG. 1, the MTBE production unit 56 can have a MTBE output stream 14 that can comprise mostly MTBE. For example, the MTBE output stream 14 can comprise greater than or equal to 80 wt % MTBE, for example, greater than or equal to 90 wt % MTBE, for example, greater than or equal to 98 wt % MTBE.

As shown in FIG. 1, the first 1-butene stream 6 and the second 1-butene stream 10 can be fed to a fuel additive production unit 55, such as a C4 alcohol production unit. The fuel additive production unit 55 can have additional inputs depending on the desired fuel additive. For example, a water stream 9 can additionally be fed to the fuel additive production unit 55. It can be desirable to use de-ionized water for the hydration reaction of the olefin with water. The fuel additive production unit 55 can have two or more outputs including, for example, a purge stream 12 and a fuel additive stream 8, for example a C4 alcohol stream 8. The purge stream 12 can include, for example, isobutane, 1-butene, 2-butene, or a combination comprising at least one of the foregoing. The fuel additive stream 8 can comprise 1-butanol, 2-butanol, tert-butyl alcohol, C4-dimer, or a combination comprising at least one of the foregoing. For example, the final fuel additive products of fuel additive stream 8 can have levels of the C4-dimer comprising trimethyl-pentane, di-isobutene, 2,2,4 trimethyl-pentane, 2,3,3 trimethyl-pentane, or a combination comprising at least one of the foregoing in an amount of 0.01 wt % to 50 wt %, for example, 0.1 to 20 wt %, based on the total weight of the fuel additive, for example the ethers such as di-isobutyl ether, di-sec-butyl ether for example, 0.1 to 20 wt %.

The purge stream 12 along with a portion of the n-butane stream 11 and a portion of the isobutane stream 4 can be fed to a total hydrogenation unit 57. The total hydrogenation unit 57 can have one or more outputs. For example, the total hydrogenation unit 57 can output a recycle stream 13. The recycle stream 13 from the total hydrogenation unit 57 can comprise, for example, n-butane, isobutane, and other alkanes. As shown in FIG. 1, this recycle stream 13 can be recycled to the feedstock stream 1 of the system 100. The steam cracker unit 50 can additionally have an ethylene and propylene output stream (not shown).

The cracking process that is contemplated by the present process is not particularly limited and can be performed in accordance with a cracking process used in the petrochemical arts, such as steam cracking. Generally, steam cracking is a process by which saturated hydrocarbons are broken down into smaller, often unsaturated, hydrocarbons. Steam cracking results in the conversion of heavier materials into lower molecular weight products that can be separated into streams of similar sized hydrocarbons. For instance, steam cracking can be used to produce a C4 stream containing a mixture of different C4 species, including n-butane, isobutane, and isomeric butenes (e.g., 1-butene, cis- and trans-2-butene, and isobutene), and 1,3-butadiene. In addition, such C4 streams may contain one or more other chemical species, non-limiting examples of which include ethyl acetylene, dimethyl acetylene, vinyl acetylene, and diacetylene. The products obtained can depend on the composition of the feed, the hydrocarbon-to-steam ratio, and/or on the cracking temperature and furnace residence time.

The fuel additive product can comprise 1-butanol, 2-butanol, tert-butyl alcohol, di-isobutene, C4-dimer, or a combination comprising at least one of the foregoing, for example, the C4-dimer can comprise di-isobutene, 2,2,4 trimethyl-pentane, 2,3,3 trimethyl-pentane, or a combination comprising at least one of the foregoing. The fuel additive product can comprise greater than or equal to 0.01 wt %, for example, 5 wt %, for example, greater than or equal to 10 wt %, for example, greater than or equal to 15 wt %, for example, greater than or equal to 20 wt %, for example, greater than or equal to 50 wt %, for example, 0.01 wt % to 50 wt % trimethyl-pentane. An octane number of the fuel additive product can be greater than or equal to 80 according to the Anti-Knock Index, for example, greater than or equal to 85, for example, greater than or equal to 87, for example, greater than or equal to 90, for example, greater than or equal to 93 for example, greater than or equal to 95.

The octane number is a standard measurement used to gauge the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Anti-Knock Index is measured by adding the research octane number (RON) and the motor octane number (MON) and dividing by two, e.g., (RON+MON)/2. The Research Octane Number is determined by running the fuel in a test engine at a speed of 600 revolutions per minute with a variable compression ratio under controlled conditions, and comparing the results with those for mixtures of iso-octane and n-heptane. Motor Octane Number is determined by testing a similar test engine to that used in determining the Research Octane Number but at a speed of 900 revolutions per minute with a preheated fuel mixture, higher engine speed, and variable ignition timing. Depending on the composition, the Motor Octane Number can be 8 to 12 units lower than the Research Octane Number. The research octane number can be greater than or equal to 88, for example, greater than or equal to 91, for example, greater than or equal to 93, greater than equal 95, greater than equal to 100. The motor octane number can be greater than or equal to 82, for example, greater than or equal to 89, for example, greater than or equal to 90, for example, greater than or equal to 93. Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by the test method ASTM D-323, which measures the vapor pressure of gasoline, volatile crude oil, and other volatile petroleum products, except for liquefied petroleum gases. Reid vapor pressure is measured in KiloPascals and represents a relative pressure to atmospheric pressure since ASTM D-323 measures the gauge pressure of the sample in a non-evacuated chamber. High levels of vaporization are desired for winter starting and operation and lower levels are desirable in avoiding vapor lock during summer heat. Fuel generally cannot be pumped when vapor is present in the fuel line, and winter starting can be difficult when liquid gasoline in the combustion chambers has not vaporized. This means that the Reid vapor pressure is changed accordingly by oil producers seasonally to maintain gasoline engine reliability.

The Reid vapor pressure of the fuel additive product of the present disclosure can be less than or equal to 55.16 kiloPascals, for example, 5 kiloPascals to 55 kiloPascals, for example, 5 kiloPascals to 40 kiloPascals. The Reid vapor pressure can vary during winter and summer conditions such that the pressure can be at the higher end of the values during the winter and at the lower end of the values during the summer.

The processes disclosed herein include at least the following aspects:

Aspect 1: A method for the production of a fuel additive, comprising: passing a hydrocarbon stream comprising crude mixed C4 hydrocarbons from one or more crackers through a first hydrogenation unit to convert butadiene components to 1-butene and 2-butene to produce a first product stream; passing the first product stream from the first hydrogenation unit to a first methyl tert-butyl ether synthesis unit forming methyl tert-butyl ether and a byproduct stream; passing the byproduct stream through a first distillation unit to separate the byproduct stream into at least three streams including a first 1-butene stream, an isobutane stream, and a 2-butene and n-butane stream; forming a second product stream by passing the 2-butene and n-butane stream to a selective conversion unit to transform the 2-butene to 1-butene; passing the second product stream into a second distillation unit to separate the n-butane from the 1-butene to form an n-butane stream and a second 1-butene stream; passing the second 1-butene stream to a fuel additive production unit to form the fuel additive; and passing the first 1-butene stream to the fuel additive production unit to form the fuel additive.

Aspect 2: The method of Aspect 1, wherein the hydrocarbon stream comprises ethyl acetylene, vinyl acetylene, 1,3-butadiene, 1,2-butadiene, isobutene, cis-2-butene, trans-2-butene, 1-butene, isobutane, n-butane, or a combination comprising at least one of the foregoing.

Aspect 3: The method of Aspect 1 or Aspect 2, wherein the hydrocarbon stream is a portion of an effluent from an olefins production plant.

Aspect 4: The method of any of the preceding aspects, wherein the hydrocarbon stream is a stream from a cracker unit.

Aspect 5: The method of any of the preceding aspects, wherein greater than or equal to 90 wt % of butadiene present in the hydrocarbon stream is converted to 1-butene and/or 2-butene within the first hydrogenation unit.

Aspect 6: The method of any of the preceding aspects, wherein the isobutene stream comprises at least 0.1 wt % butenes.

Aspect 7: The method of any of the preceding aspects, further comprising passing the isobutane stream to a methyl tert-butyl ether production unit.

Aspect 8: The method of any of the preceding aspects, further comprising passing additional isobutane to the methyl tert-butyl ether production unit.

Aspect 9: The method of any of the preceding aspects, wherein the methyl tert-butyl ether production unit comprises dehydrogenation and methyl tert-butyl ether synthesis units.

Aspect 10: The method of any of the preceding aspects, further comprising recycling the isobutane to a cracker unit to produce ethylene and propylene.

Aspect 11: The method of any of the preceding aspects, further comprising passing the n-butane stream to a methyl tert-butyl ether production unit.

Aspect 12: The method of any of the preceding aspects, wherein the methyl tert-butyl ether production unit comprises deisobutanizer, isomerization, dehydrogenation and methyl tert-butyl ether synthesis units.

Aspect 13: The method of any of the preceding aspects, further comprising recycling the n-butane stream to a cracker unit to produce ethylene and propylene.

Aspect 14: The method of any of the preceding aspects, wherein the selective conversion unit is a selective hydrogenation unit.

Aspect 15: The method of any of the preceding aspects, wherein the fuel additive comprises 1-butanol, 2-butanol, tert-butyl alcohol, C4-dimer, trimethyl-pentane, di-isobutene, 2,2,4 trimethyl-pentane, 2,3,3 trimethyl-pentane, or a combination comprising at least one of the foregoing.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

"Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

As used herein, the term "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxys; $C_{6-10}$ aryloxy such as phenoxy; $C_{1-6}$ alkylthio; $C_{1-6}$ or $C_{1-3}$ alkylsulfinyl; C1-6 or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); C7-19 arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

The terms "fuel oxygenates," "gasoline oxygenates" and simply "oxygenates" refer to a class of gasoline additives that contain one or more oxygen atoms and are designed to improve the octane rating of gasoline increasing the oxygen content of the gasoline. Most oxygenates are either alcohols or ethers, for example methanol (MeOH), ethanol (EtOH), isopropyl alcohol (IPA), n-propyl alcohol (NPrOH), isobutanol (IBA), n-butanol (BuOH), sec-butyl alcohol (SBA), tert-butyl alcohol (TBA) or gasoline grade tert-butyl alcohol (GTBA), tert-amyl alcohol (TAA) or tert-pentanol, methyl tert-butyl ether (MTBE), ethyl tert-butyl ether (ETBE), tert-amyl methyl ether (TAME), tert-amyl ethyl ether (TAEE), tert-hexyl methyl ether (THEME) and diisopropyl ether (DIPE). These oxygenates can be produced by any known and acceptable chemical and biological reactions that are known in the art, for example, chemical reaction between isobutene and methanol or ethanol to produce MTBE or ETBE respectively, microbial fermentation of sugars to produce bio-ethanol, and the like. Production processes can further include purification, distillation, or dehydration steps to increase purity and to remove water.

"Fuel" refers to one or more alcohols, one or more hydrocarbons, one or more fatty esters, or a mixture thereof. In some embodiments, liquid alcohols are used. The fuel disclosed herein can be used to power internal combustion engines such as reciprocating engines (e.g., gasoline engines and diesel engines), Wankel engines, jet engines, some rocket engines, missile engines, and gas turbine engines. In some embodiments, the fuel comprises a mixture of alcohols such as butanol and pentanol.

"Fuel additive" refers to a minor fuel component such as chemical components added to fuels to alter the properties of the fuel, e.g., to improve engine performance, combustion efficiency, fuel handling, fuel stability, or for contaminant control. Types of additives include, but are not limited to, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof. The term "conventional additives" refers to fuel additives known to the skilled artisan, such as those described herein.

A composition that is "substantially free" of a compound refers to a composition containing less than 20%, less than 10%, less than 5%, less than 4%, less than 3%, less than 2%, less than 1%, less than 0.5%, less than 0.1%, or less than 0.01% of the compound, based on the total volume or weight of the composition.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for the production of a fuel additive, comprising:
    passing a hydrocarbon stream comprising crude mixed C4 hydrocarbons from one or more cracker units through a first hydrogenation unit to convert butadiene components to 1-butene and 2-butene to produce a first product stream;
    passing the first product stream from the first hydrogenation unit to a methyl tert-butyl ether synthesis unit forming methyl tert-butyl ether and a byproduct stream;
    passing the byproduct stream through a first distillation unit to separate the byproduct stream into at least three streams including a first 1-butene stream, an isobutane stream, and a 2-butene and n-butane stream;
    forming a second product stream by passing the 2-butene and n-butane stream to a selective conversion unit to transform the 2-butene to 1-butene;
    passing the second product stream into a second distillation unit to separate the n-butane from the 1-butene to form an n-butane stream and a second 1-butene stream;
    passing the second 1-butene stream to a fuel additive production unit to form the fuel additive; and
    passing the first 1-butene stream to the fuel additive production unit to form the fuel additive.

2. The method of claim 1, wherein the hydrocarbon stream comprises ethyl acetylene, vinyl acetylene, 1,3-butadiene, 1,2-butadiene, isobutene, cis-2-butene, trans-2-butene, 1-butene, isobutane, n-butane, or a combination comprising at least one of the foregoing.

3. The method of claim 1, wherein the hydrocarbon stream is a portion of an effluent from an olefins production plant.

4. The method of claim 1, wherein the hydrocarbon stream is a stream from a cracker unit.

5. The method of claim 1, wherein greater than or equal to 90 wt % of butadiene present in the hydrocarbon stream is converted to 1-butene and/or 2-butene within the first hydrogenation unit.

6. The method of claim 1, wherein the isobutane stream comprises at least 0.1 wt % butenes.

7. The method of claim 1, further comprising passing the isobutane stream to a methyl tert-butyl ether production unit.

8. The method of claim 7, further comprising passing additional isobutane to the methyl tert-butyl ether production unit.

9. The method of claim 7, wherein the methyl tert-butyl ether production unit comprises dehydrogenation and methyl tert-butyl ether synthesis units.

10. The method of claim 7, further comprising passing the n-butane stream to the methyl tert-butyl ether production unit.

11. The method of claim 7, wherein the methyl tert-butyl ether production unit comprises deisobutanizer, isomerization, dehydrogenation and methyl tert-butyl ether synthesis units.

12. The method of claim 1, further comprising recycling the isobutane to a cracker unit to produce ethylene and propylene.

13. The method of claim 1, further comprising recycling the n-butane stream to a cracker unit to produce ethylene and propylene.

14. The method of claim 1, wherein the selective conversion unit is a selective hydrogenation unit.

15. The method of claim 1, wherein the fuel additive comprises 1-butanol, 2-butanol, tert-butyl alcohol, C4-dimer, trimethyl-pentane, di-isobutene, 2,2,4 trimethyl-pentane, 2,3,3 trimethyl-pentane, or a combination comprising at least one of the foregoing.

* * * * *